US007235239B2

(12) United States Patent
Guegler et al.

(10) Patent No.: US 7,235,239 B2
(45) Date of Patent: Jun. 26, 2007

(54) ANTIBODIES TO A CHEMOKINE EXPRESSED IN INFLAMED ADENOID

(75) Inventors: Karl J Guegler, Menlo Park, CA (US); Phillip R Hawkins, Mountain View, CA (US); Craig G Wilde, deceased, late of Sunnyvale, CA (US); Jeffrey J Seilhamer, deceased, late of Los Altos Hills, CA (US)

(73) Assignee: Incyte Incorporation, Wilmington, DE (US)

( * ) Notice: Subject to any disclaimer, the term of this patent is extended or adjusted under 35 U.S.C. 154(b) by 24 days.

(21) Appl. No.: 10/700,314

(22) Filed: Oct. 28, 2003

(65) Prior Publication Data

US 2004/0086975 A1     May 6, 2004

Related U.S. Application Data

(62) Division of application No. 09/588,044, filed on Jun. 5, 2000, now Pat. No. 6,692,920, which is a division of application No. 09/203,235, filed on Dec. 1, 1998, now Pat. No. 6,071,701, which is a division of application No. 08/862,607, filed on May 23, 1997, now Pat. No. 5,844,084, which is a division of application No. 08/352,324, filed on Dec. 7, 1994, now Pat. No. 5,633,149.

(51) Int. Cl.
*A61K 39/395* (2006.01)
*C07K 16/24* (2006.01)

(52) U.S. Cl. ............................... 424/145.1; 424/139.1; 424/141.1; 424/1.49

(58) Field of Classification Search .................... None
See application file for complete search history.

(56) References Cited

U.S. PATENT DOCUMENTS

| | | | |
|---|---|---|---|
| 3,996,345 A | 12/1976 | Ullman et al. | |
| 4,275,149 A | 6/1981 | Litman et al. | |
| 4,277,437 A | 7/1981 | Maggio | |
| 4,816,567 A | 3/1989 | Cabilly et al. | |
| 5,011,912 A | 4/1991 | Hopp et al. | |
| 5,094,941 A * | 3/1992 | Hart ............................ | 435/7.9 |
| 5,126,434 A * | 6/1992 | Osawa et al. ............. | 530/387.9 |
| 6,692,920 B1 * | 2/2004 | Guegler et al. .............. | 435/7.1 |

OTHER PUBLICATIONS

Harlow and Lane (1988) Antibodies, A Laboratory Manual. Cold Spring Harbor Laboratory, Chapter 5, p. 76.*
Rieger et al. Glossary of Genetics and Cytogenetics, Fourth Edition, Springer-Verlag, pp. 16-19.*
Mikayama et al. Proc. Natl. Acad. Sci. USA. vol. 90, pp. 10056-10060.*
Voet et al. Biochemistry. John Wiley & Sons, Inc., pp. 126-128 and 228-234.*
Vilcek, J. et al., Immunology of Cytokines *The Cytokine Handbook* Academic Press, Copyright 1991, Chapter 1, pp. 1-17.
Shaw, A.R., "Molecular Biology of Cytokines" *The Cytokine Handbook*, Academic Press, Copyright 1991, Chapter 2, pp. 20-46.
Banchereau, J., "Interleukin-4" *The Cytokine Handbook*, Academic Press, Copyright 1991, Chapter 6, pp. 120-148.
Schall, T.J., "The Chemokines" *The Chemokine Handbook*, Academic Press, 1994, Sep. 19-20, Second Edition, pp. 180-272.
Uhlmann et al., "Antisense Oligonucleotides: a New Therapeutic Principle" *Chemical Reviews* 90(4) :554-584 (1990).
Cotten et al., "Ribozyme Mediated Destruction of RNA in vivo" *The EMBO Journal* 8(12) :3861-3866 (1989).
Ledley, F.D., "Clinical Consideration in the Design of Protocols for Somatic Gene Therapy" *Human Gene Therapy* 2:77-82 (1991).
Anderson, W.F., "Prospects for Human Gene Therapy" *Science* 226:401-409 (1984).
Opdenakker et al., "The Human MCP-3 Gene (SCYA7): Cloning, Sequence Analysis, and Assignment to the C—C Chemokine Gene Cluster on Chromosome 17q11.2-q12" *Genomics* 21:403-408 (1994).
Diamond et al., "Novel delayed-early and highly insulin-induced growth response genes. Identification of HRS, a potential regulator of alternative pre-mRNA splicing" *Journal of Biol. Chem.* 268(20):15185-15192 (1993).
Derynck et al., (1990) Biochemistry vol. 29, pp. 10225-10233.
Bork et al., Trends in Genetics, vol. 12, No. 10, pp. 425-427 (1996).
Doerks et al., Trends in Genetics, vol. 14, No. 6, pp. 248-250 (1998).
Brenner et al., Trends in Genetics, vol. 15, No. 8, pp. 132-133 (1999).
Schall, T. et al., "Chemokines, leukocyte trafficking, and inflammation", Current Opinion in Immunology 1994, 6:865-873.
Goodman et al., "Molecular Cloning of Porcine Alveolar Macrophage-Derived Neutrophil Chemotactic Factors I and II: Identification of Porcine IL-8 and Another Intercrine-α Protein†'‡", *Biochemistry*, vol. 31, No. 43, Nov. 3, 1992 (pp. 10483-10490).
Harlow et al., "Human Hybridomas", *Antibodies, A Laboratory Manual*, 1988 (p. 241).

(Continued)

*Primary Examiner*—Prema Mertz
(74) *Attorney, Agent, or Firm*—Foley & Lardner LLP

(57) ABSTRACT

The present invention provides nucleotide and amino acid sequences that identify and encode a novel expressed chemokine (ADEC) from inflamed adenoid tissue. The present invention also provides for antisense molecules to the nucleotide sequences which encode ADEC, expression vectors for the production of purified ADEC, antibodies capable of binding specifically to ADEC, hybridization probes or oligonucleotides for the detection of ADEC-encoding nucleotide sequences, genetically engineered host cells for the expression of ADEC, diagnostic tests for inflammation or disease based on ADEC-encoding nucleic acid molecules or antibodies capable of binding specifically to ADEC.

10 Claims, 4 Drawing Sheets

OTHER PUBLICATIONS

Lin et al., "Regulation of Interleukin-8 Expression in Porcine Alveolar Macrophages by Bacterial Lipopolysaccharide", *The Journal of Biological Chemistry*, vol. 269, No. 1, Jan. 7, 1994 (pp. 77-85).

Seow et al., "Cloning, sequencing, expression and inflammatory activity in skin of ovine interleukin-8", *Immunology and Cell Biology*, vol. 72, Issue 5, Oct. 1994 (pp. 398-405).

BLAST results for alignment of SEQ ID No. 2 and MCP-4, at National Center for Biotechnology Informatin database (2 pp.).

BLAST results for alignment of SEQ ID No. 1 and the gene for MCP-4, at National Center for Biotechnology Information database (2 pp.).

Huse et al., "Generation of a Large Combinatorial Library of the Immunoglobulin Repertoire in Phage Lambda", *Science*, vol. 246, Dec. 8, 1989 (pp. 1275-1281).

Orlandi et al., "Cloning immunoglobulin variable domains for expression by the polymerase chain reaction", *Proc. Natl. Acad. Sci.*, vol. 86, May 1989 (pp. 3833-3837).

Sambrook et al., Molecular Cloning: A Laboratory Manual, $2^{nd}$ Ed, Cold Spring Harbor, N.Y. (4 pp.).

"Synopsis of Application of Written Description Guidelines" (66 pp).

Winter et al., "Man-made antibodies", *Nature*, vol. 349, Jan. 24, 1991 (pp. 293-299).

* cited by examiner

```
                9                18                27                36                45                54
5' ATG AAG TTC ATC TCG ACA TCT CTG CTT CTC ATG CTG CTG GTC AGC AGC CTC TCT
   M   K   F   I   S   T   S   L   L   L   M   L   L   V   S   S   L   S 63               72                81                90                99               108
   CCA GTC CAA GGT GTT CTG GAG GTC TAT TAC ACA AGC TTG AGG TGT AGA TGT GTC
   P   V   Q   G   V   L   E   V   Y   Y   T   S   L   R   C   R   C   V 117              126               135              144                153              162
   CAA GAG AGC TCA GTC TTT ATC CCT AGA CGC TTC ATT GAT CGA ATT CAA ATC TTG
   Q   E   S   S   V   F   I   P   R   R   F   I   D   R   I   Q   I   L 171              180               189              198                207              216
   CCC CGT GGG AAT GGT TGT CCA AGA AAA GAA ATC ATA GTC TGG AAG AAG AAC AAG
   P   R   G   N   G   C   P   R   K   E   I   I   V   W   K   K   N   K 225              234               243              252                261              270
   TCA ATT GTG TGT GTG GAC CCT CAA GCT GAA TGG ATA CAA AGA ATG ATG GAA GTA
   S   I   V   C   V   D   P   Q   A   E   W   I   Q   R   M   M   E   V 279              288               297              306                315              324
   TTG ACA AAA AGA AGT TCT TCA ACT CTA CCA GTT CCA GTG TTT AAG AGA AAG ATT
   L   T   K   R   S   S   S   T   L   P   V   P   V   F   K   R   K   I

CCC TGA  3'
   P   *
```

FIG. 1

```
         10                  20                 30
1   M S L L S S R A A R V P G P S S - L C A L L V L L L L T   ENA78
1   M A - - - - R A T L S A A P S N P R L L R V A L L L L L V   GRO-beta
1   M A - - - - H A T L S A A P S N P R L L R V A L L L L L V   GRO-gamma
1   M T - - - - - - - - - - - - - - S K L A V A L L A A F L I   IL-8
1   M A - - - - R A A L S A A P S N P R L L R V A L L L L L V   MGSA
1   M S - - - - S A A G F C A S R P G L L F L G L L L L P L V   PF4
1   M K F I S T S - - - - - - - - - - - - - - - - L L L M L L   ADEC 40                 50                 60
30  Q P G P I A S A G P A A V L R E L R C V C L Q T T - Q G V   ENA78
27  A A S R R A A G A P L A T - - - E L R C Q C L Q T L - Q G I   GRO-beta
27  G - S R R A A G A S V V T - - - E L R C Q C L Q T L - Q G I   GRO-gamma
16  S A A L C - E G A V L P R S A K E L R C Q C I K T Y S K P F   IL-8
27  A A G R R A A G A S V A T - - - E L R C Q C L Q T L - Q G I   MGSA
26  V A F A S A E A E E D G - - - D L Q C L C V K T T - S Q V   PF4
14  V S S L S P V Q G V L E V Y Y T S L R C R C V Q E S S V F I   ADEC 70                 80                 90
59  H P K M I S N L Q V F A I G P Q C S K V E V V A S L K N G K   ENA78
53  H L K N I Q S V K V K S P G P H C A Q T E V I A T L K N G Q   GRO-beta
52  H L K N I Q S V N V R S P G P H C A Q T E V I A T L K N G K   GRO-gamma
45  H P K F I K E L R V I E S G P H C A N T E I I V K L S D G R   IL-8
53  H P K N I Q S V N V K S P G P H C A Q T E V I A T L K N G R   MGSA
51  R P R H I T S L E V I K A G P H C P T A Q L I A T L K N G R   PF4
44  P R R F I D R I Q I L P R G N G C P R K E I I V W K K N K S   ADEC 100                110                120
89  E I C L D P E A P F L K K V I Q K I L D G G N K E - - - - -   ENA78
83  K A C L N P A S P M V K K I I E K M L K N G - K S - - - - -   GRO-beta
82  K A C L N P A S P M V Q K I I E K I L N K G - S T - - - - -   GRO-gamma
75  E L C L D P K E N W V Q R V V E K F L K R A E N S           IL-8
83  K A C L N P A S P I V K K I I E K M L N S D - K S - - - - -   MGSA
81  K I C L D L Q A P L Y K K I I K K L L E S                   PF4
74  I V C V D P Q A E W I Q R M M E V L R K R S S S T L P V P V   ADEC 114  - - - - - N                                                ENA78
107  - - - - - N                                                GRO-beta
106  - - - - - N                                                GRO-gamma
99                                                              IL-8
107  - - - - - N                                                MGSA
101                                                             PF4
104  F K R K I P                                                ADEC
```

DECORATION 'DECORATION #1': BOX RESIDUES THAT MATCH THE CONSENSUS EXACTLY.

FIG. 2

SEQUENCE LISTING

<160> NUMBER OF SEQ ID NOS: 2

<210> SEQ ID NO 1
<211> LENGTH: 330
<212> TYPE: DNA
<213> ORGANISM: Homo sapiens
<220> FEATURE:
<221> NAME/KEY: misc_feature
<223> OTHER INFORMATION: Incyte ID No: 020293CB1

<400> SEQUENCE: 1

| | | | | | |
|---|---|---|---|---|---|
| atgaagttca | tctcgacatc | tctgcttctc | atgctgctgg | tcagcagcct | ctctccagtc | 60 |
| caaggtgttc | tggaggtcta | ttacacaagc | ttgaggtgta | gatgtgtcca | agagagctca | 120 |
| gtctttatcc | ctagacgctt | cattgatcga | attcaaatct | tgccccgtgg | gaatggttgt | 180 |
| ccaagaaaag | aaatcatagt | ctggaagaag | aacaagtcaa | ttgtgtgtgt | ggaccctcaa | 240 |
| gctgaatgga | tacaaagaat | gatggaagta | ttgagaaaaa | gaagttcttc | aactctacca | 300 |
| gttccagtgt | ttaagagaaa | gattccctga | | | | 330 |

<210> SEQ ID NO 2
<211> LENGTH: 109
<212> TYPE: PRT
<213> ORGANISM: Homo sapiens
<220> FEATURE:
<221> NAME/KEY: misc_feature
<223> OTHER INFORMATION: Incyte ID No: 020293CD1

<400> SEQUENCE: 2

Met Lys Phe Ile Ser Thr Ser Leu Leu Met Leu Leu Val Ser
1               5                   10                  15

Ser Leu Ser Pro Val Gln Gly Val Leu Glu Val Tyr Tyr Thr Ser
                20              25                  30

Leu Arg Cys Arg Cys Val Gln Glu Ser Ser Val Phe Ile Pro Arg
                35                  40                  45

Arg Phe Ile Asp Arg Ile Gln Ile Leu Pro Arg Gly Asn Gly Cys
                50                  55                  60

Pro Arg Lys Glu Ile Ile Val Trp Lys Lys Asn Lys Ser Ile Val
                65                  70                  75

Cys Val Asp Pro Gln Ala Glu Trp Ile Gln Arg Met Met Glu Val
                80                  85                  90

Leu Arg Lys Arg Ser Ser Ser Thr Leu Pro Val Pro Val Phe Lys
                95                  100                 105

Arg Lys Ile Pro

ANTIBODIES TO A CHEMOKINE EXPRESSED IN INFLAMED ADENOID

This application is a divisional application of U.S. application Ser. No. 09/588,044, filed Jun. 5, 2000 now U.S. Pat. No. 6,692,920, entitled ANTIBODIES TO A CHEMOKINE EXPRESSED IN INFLAMED ADENOID (as amended), which is a divisional application of U.S. application Ser. No. 09/203,235, filed Dec. 1, 1998, and issued on Jun. 6, 2000 as U.S. Pat. No. 6,071,701, entitled METHOD OF DETECTION FOR A POLYNUCLEOTIDE ENCODING CHEMOKINE EXPRESSED IN INFLAMED ADENOID, which is a divisional application of U.S. application Ser. No. 08/862,607, filed May 23, 1997, and issued on Dec. 1, 1998 as U.S. Pat. No. 5,844,084, entitled CHEMOKINE EXPRESSED IN INFLAMED ADENOID, which is a divisional application of U.S. application Ser. No. 08/352,324, filed Dec. 7, 1994, and issued on May 27, 1997 as U.S. Pat. No. 5,633,149, entitled POLYNUCLEOTIDE ENCODING NOVEL CHEMOKINE EXPRESSED IN INFLAMED ADENOID. All of these patents and applications are hereby expressly incorporated herein by reference.

BACKGROUND OF THE INVENTION

Leukocytes including monocytes, macrophages, basophils, and eosinophils play important roles in the pathological mechanisms initiated by T and/or B lymphocytes. Macrophages, in particular, produce powerful oxidants and proteases which contribute to tissue destruction and secrete a range of cytokines which recruit and activate other inflammatory cells.

The investigation of the critical, regulatory processes by which white cells proceed to their appropriate destination and interact with other cells is underway. The current model of leukocyte movement or trafficking from the blood to injured or inflamed tissues comprises the following steps. The first step is the rolling adhesion of the leukocyte along the endothelial cells of the blood vessel wall. This movement is mediated by transient interactions between selectins and their ligands. A second step involves cell activation which promotes a more stable leukocyte-endothelial cell interaction mediated by the integrins and their ligands. This stronger, more stable adhesion precipitates the final steps—leukocyte diapedesis and extravasation into the tissues.

The chemokine family of polypeptide cytokines, also known as intercrines, possesses the cellular specificity required to explain leukocyte trafficking in different inflammatory situations. First, chemokines mediate the expression of particular adhesion molecules on endothelial cells; and second, they generate gradients of chemoattractant factors which activate specific cell types. In addition, the chemokines stimulate the proliferation of specific cell types and regulate the activation of cells which bear specific receptors. Both of these activities demonstrate a high degree of target cell specificity.

The chemokines are small polypeptides, generally about 70–100 amino acids (aa) in length, 8–11 kD in molecular weight and active over a 1–100 ng/ml concentration range. Initially, they were isolated and purified from inflamed tissues and characterized relative to their bioactivity. More recently, chemokines have been discovered through molecular cloning techniques and characterized by structural as well as functional analysis.

The chemokines are related through a four cysteine motif which is based primarily on the spacing of the first two cysteine residues in the mature molecule. Currently the chemokines are assigned to one of two families, the C-X-C chemokines ($\alpha$) and the C-C chemokines ($\beta$). Although exceptions exist, the C-X-C chemokines generally activate neutrophils and fibroblasts while the C-C chemokines act on a more diverse group of target cells which include monocytes/macrophages, basophils, eosinophils, T lymphocytes and others. The known chemokines of both families are synthesized by many diverse cell types as reviewed in Thomson A. (1994) The Cytokine Handbook, 2nd Ed., Academic Press, N.Y. The two groups of chemokines will be described in turn.

The archetypal and most extensively studied C-X-C chemokine is platelet factor 4 (PF4). This 70 aa protein displays the definitive four cysteines and is released along with platelet derived growth factor (PDGF), transforming growth factor $\beta$ (TGF-$\beta$) and $\beta$-thromboglobulin ($\beta$-TG) from the granules of stimulated platelets. This homotetrameric molecule shares structural similarity with interleukin-8 (IL-8), induces the migration of fibroblasts, neutrophils and monocytes, and binds heparin. PF4 provides the biological model for a link among thrombosis, inflammation, and wound healing.

Other chemokines found in the platelet a granule include $\beta$-TG, connective tissue activating protein III (CTAP-III) and neutrophil activating peptide 2 (NAP-2). All three peptides are derived from the differential processing of a precursor molecule, platelet basic protein (PBP). $\beta$-TG is an 81 aa, highly basic protein which influences the migration of fibroblasts but has no effect on neutrophils or monocytes. CTAP-III is 85 aa long, and aa 4–85 are identical to $\beta$-TG. Since CTAP-III is the primary protein in the a granule and its role as a purified protein has not been elucidated, it may be a secondary precursor, inactive until further processed. NAP-2 appears to attract neutrophils but not monocytes.

Nonplatelet C-X-C chemokines include IL-8, $\gamma$ interferon inducible protein (IP-10), melanocyte growth stimulatory activity (MGSA or gro) proteins, epithelial derived neutrophil attractant-78 (ENA-78), granulocyte chemotactic protein-2 (GPC-2) and stromal cell-derived factors-1$\alpha$ and 1$\beta$ (SDF-1$\alpha$ and -1$\beta$). IL-8 (also known as NAP-1) is secreted by monocytes/macrophages, neutrophils, fibroblasts, endothelial cells, keratinocytes and T lymphocytes in response to proinflammatory cytokines, IL-1 and 3, IFN-$\gamma$ and TNF, as well as endotoxins, mitogens, particulates, bacteria and viruses. IL-8 stimulates acute inflammation including the upregulation of both neutrophil adhesion and keratinocyte growth and the downregulation of histamine production by basophils.

IP-10 is a 10 kD protein of undefined function whose mRNA has been found in monocytes, fibroblasts and endothelial cells. Monocytes, keratinocytes and activated T cells secrete IP-10 protein which has been localized to sites of delayed hypersensitivity reactions. The cDNA of MGSA/gro a produces a 15 kD protein which appears in fibroblasts. Its transcription is growth related, and it functions as an autocrine growth factor. The distinct and non-allelic forms, gro $\beta$ and gro $\gamma$, are 90% and 86% identical to gro $\alpha$, respectively. Recombinant gro a proteins attract and activate neutrophils. ENA-78 was purified from supernatants of lung alveolar cells. Like gro $\alpha$, it attracts and activates neutrophils in vitro.

GCP-2 is a 6 kD protein isolated from the supernatants of osteosarcoma cells. GCP-2 exists in various N-terminally truncated forms, and it attracts and activates neutrophils in vitro and causes granulocyte accumulation in vivo. SDF-1$\alpha$ and -1$\beta$ are newly isolated cDNAs which encode secreted molecules and type I membrane proteins.

Current techniques for diagnosis of abnormalities in inflamed or diseased tissues mainly rely on observation of clinical symptoms or serological analyses of body tissues or fluids for hormones, polypeptides or various metabolites. Patients often manifest no clinical symptoms at early stages of disease or tumor development. Furthermore, serological analyses do not always differentiate between invasive diseases and genetic syndromes which have overlapping or very similar ranges. Thus, development of new diagnostic techniques comprising small molecules such as the expressed chemokines are important to provide for early and accurate diagnoses, to give a better understanding of molecular pathogenesis, and to use in the development of effective therapies.

The chemokine molecules were reviewed in Schall T J (1994) Chemotactic Cytokines: Targets for Therapeutic Development, International Business Communications, Southborough, Mass., pp 180–270; and in Paul W E (1993) Fundamental Immunology, 3rd Ed., Raven Press, NYC, pp 822–826.

SUMMARY OF THE INVENTION

The subject invention provides a nucleotide sequence which uniquely encodes a novel human protein from inflamed adenoid. The new gene, which is known as adenoid expressed chemokine, or adec (Incyte Clone No. 20293), encodes a polypeptide designated ADEC, of the C-X-C chemokine family. The invention also comprises diagnostic tests for inflammatory conditions which include the steps of testing a sample or an extract thereof with adec DNA, fragments or oligomers thereof. Aspects of the invention include the antisense DNAs of adec; cloning or expression vectors containing adec; host cells or organisms transformed with expression vectors containing adec; a method for the production and recovery of purified ADEC from host cells; and purified ADEC.

DESCRIPTION OF THE FIGURES

FIG. 1 displays the nucleotide sequence for adec and the predicted amino acid (aa) sequence of the adenoid expressed chemokine, ADEC.

FIG. 2 shows the aa alignment of ADEC with other human chemokines of the C-X-C family. Alignments shown were produced using the multisequence alignment program of DNASTAR software (DNASTAR Inc, Madison, Wis.).

DETAILED DESCRIPTION OF THE INVENTION

Definitions

Figure 3:
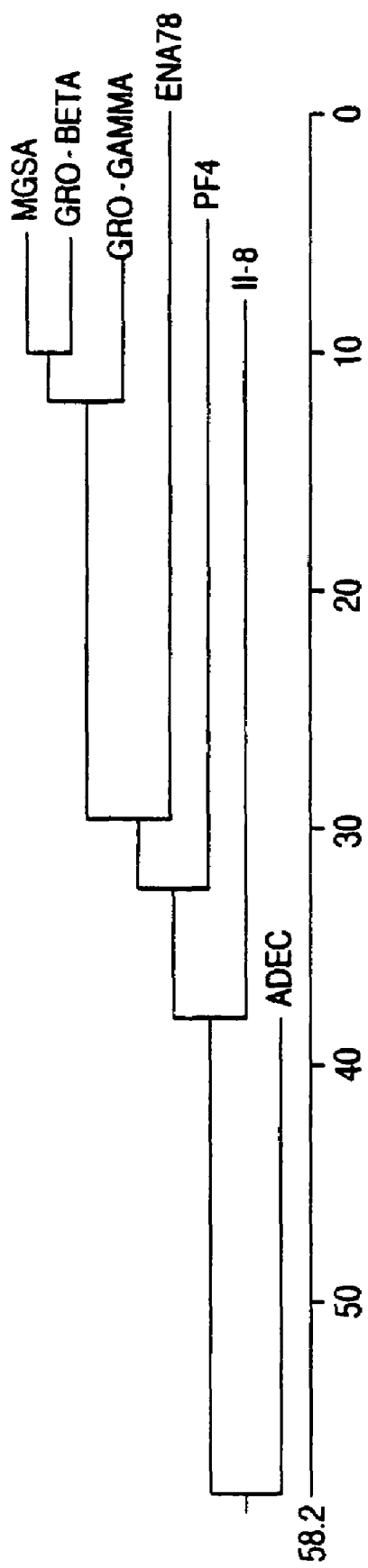
FIG. 3 shows a relatedness tree of human C-X-C chemokines. The phylogenetic tree was generated by phylogenetic tree program of DNASTAR software (DNASTAR Inc, Madison, Wis.) using the Clustal method with the PAM250 residue weight table.

As used herein, "adenoid expressed chemokine" or ADEC, refers to a polypeptide, a naturally occurring ADEC or active fragments thereof, which is encoded by an mRNA transcribed from ADEC cDNA of a particular SEQ ID NO.

"Active" refers to those forms of ADEC which retain the biologic and/or immunologic activities of naturally occurring ADEC.

"Naturally occurring ADEC" refers to ADEC produced by human cells that have not been genetically engineered and specifically contemplates various ADEC forms arising from post-translational modifications of the polypeptide including but not limited to acetylation, carboxylation, glycosylation, phosphorylation, lipidation and acylation.

"Derivative" refers to polypeptides derived from naturally occurring ADEC by chemical modifications such as ubiquitination, labeling (e.g., with radionuclides, various enzymatic modifications), pegylation (derivatization with polyethylene glycol) or by insertion or substitution by chemical synthesis of aa such as ornithine, which do not normally occur in human proteins.

"Recombinant variant" refers to any polypeptide differing from naturally occurring ADEC by aa insertions, deletions, and substitutions, created using recombinant DNA techniques. Guidance in determining which aa residues may be replaced, added or deleted without abolishing activities of interest, cell adhesion and chemotaxis, may be found by comparing the sequence of the particular ADEC with that of homologous cytokines and minimizing the number of aa sequence changes made in regions of high homology.

Preferably, aa substitutions are the result of replacing one aa with another aa having similar structural and/or chemical properties, such as the replacement of a leucine with an isoleucine or valine, an aspartate with a glutamate, or a threonine with a serine, i.e., conservative aa replacements. Insertions or deletions are typically in the range of about 1 to 5 aa. The variation allowed may be experimentally determined by systematically making insertions, deletions, or substitutions of aa in ADEC using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of aa residues of at least about 5 amino acids, often at least about 7 aa, typically at least about 9 to 13 aa, and, in various embodiments, at least about 17 or more aa. To be active, ADEC polypeptide must have sufficient length to display biologic and/or immunologic activity.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules.

The present invention includes purified ADEC polypeptides from natural or recombinant sources, cells transformed with recombinant nucleic acid molecules encoding ADEC. Various methods for the isolation of the ADEC polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology, Vol. 182, Academic Press, San Diego, Calif.; and Scopes R (1982) Protein Purification: Principles and Practice, Springer-Verlag, New York, N.Y., both incorporated herein by reference.

"Recombinant" may also refer to a polynucleotide which encodes ADEC and is prepared using recombinant DNA techniques. The DNA which encodes ADEC may also include allelic or recombinant variants and mutants thereof.

"Oligonucleotides" or "nucleic acid probes" are prepared based on the cDNA sequence which encodes ADEC provided by the present invention. Oligonucleotides comprise portions of the DNA sequence having at least about 15 nucleotides, usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNA encoding ADEC is present in a cell or tissue or to isolate similar nucleic acid sequences from chromosomal DNA as described by Walsh PS et al (1992) PCR Methods Appl 1:241–250.

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, 2nd Ed, Cold Spring Harbor, N.Y.; or Ausubel F M et al (1989) Current Protocols in Molecular Biology, Vol 2, John Wiley & Sons, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, to change ligand-binding affinities, interchain affinities, or polypeptide degradation or turnover rate.

DETAILED DESCRIPTION OF THE INVENTION

The present invention provides a nucleotide sequence uniquely identifying a novel chemokine of the C-X-C family, ADEC, which is highly expressed in inflamed adenoid. Because ADEC is specifically expressed in the tissue from which it was identified and has not been found in other tissues, the nucleic acid (adec), polypeptide (ADEC) and antibodies to ADEC are useful in diagnostic tests for inflamed or diseased adenoid. Excessive expression of ADEC leads to activation of neutrophils and fibroblasts which respond by producing abundant proteases and other molecules which can lead to tissue damage or destruction. Therefore, a diagnostic test for excess expression of ADEC can accelerate diagnosis and proper treatment of inflammation before extensive tissue damage or destruction occurs.

The nucleotide sequences encoding ADEC (or their complement) have numerous applications in techniques known to those skilled in the art of molecular biology. These techniques include use as hybridization probes, use as oligomers for PCR, use for chromosome and gene mapping, use in the recombinant production of ADEC, and use in generation of anti-sense DNA or RNA, their chemical analogs and the like. Uses of nucleotides encoding ADEC disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of ADEC-encoding nucleotide sequences, some bearing minimal nucleotide sequence homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring ADEC, and all such variations are to be considered as being specifically disclosed.

Although nucleotide sequences which encode ADEC and/or ADEC variants are preferably capable of hybridizing to the nucleotide sequence of the naturally occurring ADEC gene under stringent conditions, it may be advantageous to produce nucleotide sequences encoding ADEC or ADEC derivatives possessing a substantially different codon usage. Codons can be selected to increase the rate at which expression of the polypeptide occurs in a particular prokaryotic or eukaryotic expression host in accordance with the frequency with which particular codons are utilized by the host. Other reasons for substantially altering the nucleotide sequence encoding ADEC and/or ADEC derivatives without altering the encoded aa sequence include the production of RNA transcripts having more desirable properties, e.g., a greater half-life, than transcripts produced from the naturally occurring nucleotide sequence.

Nucleotide sequences encoding ADEC may be joined to a variety of other nucleotide sequences by means of well established recombinant DNA techniques (cf. Sambrook J et al. (1989) Molecular Cloning: A Laboratory Manual, 2nd Ed, Cold Spring Harbor, N.Y.).

Useful nucleotide sequences for joining to adec include an assortment of cloning vectors, e.g., plasmids, cosmids, lambda phage derivatives, phagemids, and the like, that are known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for adec-specific nucleic acid hybridization probes capable of hybridizing with naturally occurring nucleotide sequences encoding ADEC. Such probes for the detection of similar chemokine encoding sequences should preferably contain at least 50% of the nucleotides from a C-X-C encoding sequence. The hybridization probes of the subject invention may be derived from the nucleotide sequences of the SEQ ID NO:1 or from genomic sequences including promoters, enhancer elements and introns of naturally occurring adec. Hybridization probes may be labeled by a variety of reporter groups, including radionuclides such as 32P or 35S, or enzymatic labels such as alkaline phosphatase, coupled to the probe via avidin/biotin coupling systems, and the like.

PCR as described in U.S. Pat. Nos. 4,965,188; 4,683,195; and 4,800,195 provides additional uses for oligonucleotides based upon the nucleotide sequences which encode ADEC. Such probes used in PCR may be of recombinant origin, may be chemically synthesized, or may be a mixture of both and may comprise a discrete nucleotide sequence for diagnostic use or a degenerate pool of possible sequences for identification of closely related genomic sequences.

Other means of producing adec-specific hybridization probes include the cloning of nucleic acid sequences encoding ADECs and ADEC derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding ADEC and ADEC derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the adec sequence or any portion thereof.

The nucleotide sequence can be used to construct an assay to detect inflammation and disease associated with abnormal levels of expression of ADEC. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample. If adec is present at an abnormal level, the assay indicates the presence of inflammation and/or disease.

The nucleotide sequence for adec can be used to construct hybridization probes for mapping that gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York, N.Y.

Fluorescent in situ hybridization of chromosomal preparations and other physical chromosome mapping techniques may be correlated with additional genetic map data. Examples of genetic map data can be found in O'Brien (1990) Genetic Maps: Locus Maps of Complex Genomes, Book 5: Human Maps, Cold Spring Harbor Laboratory, N.Y. Correlation between the location of adec on a physical chromosomal map and a specific disease (or predisposition to a specific disease) can help delimit the region of DNA associated with that genetic disease. The nucleotide sequence of the subject invention may be used to detect differences in gene sequence between normal, carrier and affected individuals.

Nucleotide sequences encoding ADEC may be used to produce purified ADEC using well known methods of recombinant DNA technology. Among the many publications that teach methods for the expression of genes after they have been isolated is Goeddel (1990) Gene Expression Technology, Methods in Enzymology. Vol 185, Academic Press, San Diego. ADEC may be expressed in a variety of host cells, either prokaryotic or eukaryotic. Host cells may be from species either the same or different from the species in which adec nucleotide sequences are endogenous. Advantages of producing ADEC by recombinant DNA technology include obtaining highly enriched sources of the proteins for purification and the availability of simplified purification procedures.

Cells transformed with DNA encoding ADEC may be cultured under conditions suitable for the expression of the ADEC and the recovery of the protein from the cell culture. ADEC produced by a recombinant cell may be secreted or may be contained intracellularly, depending on the particular genetic construction used. In general, it is more convenient to prepare recombinant proteins in secreted form. Purification steps depend on the nature of the production process used and the particular ADEC produced.

In addition to recombinant production, ADEC fragments may be produced by direct peptide synthesis using solid-phase techniques (cf. Stewart et al (1969) Solid-Phase Peptide Synthesis, WH Freeman Co, San Francisco; Merrifield J (1963) J Am Chem Soc 85:2149–2154).

In vitro protein synthesis may be performed using manual techniques or by automation. Automated synthesis may be achieved, for example, using a 431A peptide synthesizer (Applied Biosystems, Foster City, Calif.) in accordance with the instructions provided by the manufacturer. Various fragments of ADEC may be chemically synthesized separately and combined using chemical methods to produce the full length molecule.

ADEC for antibody induction does not need to have biological activity; however, it must be immunogenic. Peptides used to induce ADEC specific antibodies may have an aa sequence consisting of at least five aa, preferably at least 10 aa. They should mimic a portion of the aa sequence of ADEC and may contain the entire aa sequence of the naturally occurring molecule. Short stretches of ADEC aa may be fused with those of another protein such as keyhole limpet hemocyanin and the chimeric molecule used for antibody production.

Antibodies specific for ADEC may be produced by inoculation of an appropriate animal with the polypeptide or an antigenic fragment. An antibody is specific for ADEC if it is produced against an epitope of the polypeptide and binds to at least part of the natural or recombinant protein. Induction of antibodies includes not only the stimulation of an immune response by injection into animals, but also analogous steps in the production of synthetic antibodies or other specific-binding molecules such as the screening of recombinant immunoglobulin libraries (cf. Orlandi R et al (1989) Proc Natl Acad Sci USA 86:3833–3837, or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding ADEC.

An additional embodiment of the subject invention is the use of ADEC-specific antibodies, inhibitors, receptors or their analogs as bioactive agents to treat inflammation or disease of the adenoid including, but not limited to, tonsilitis, Epstein-Barr virus, Hodgkin's disease, various neoplasms or nonspecific pharyngitis. Compositions comprising the above mentioned molecules may be administered in a suitable therapeutic dose determined by any of several methodologies including clinical studies on mammalian species to determine maximal tolerable dose and on normal human subjects to determine safe dose. Additionally the bioactive agent may be complexed with a variety of well established compounds or compositions which enhance stability or pharmacological properties such as half-life. It is contemplated that the therapeutic, bioactive agent may be delivered orally via lozenges, syrups, sprays or topical application, by subcutaneous injection, airgun, etc.

The examples below are provided to illustrate the subject invention. These examples are provided by way of illustration and are not included for the purpose of limiting the invention.

EXAMPLES

I Isolation of mRNA and Construction of cDNA Libraries

The adec cDNA sequence was identified among the sequences comprising the inflamed adenoid library. This library was constructed from mixed adenoid and tonsil lymphoid tissue surgically removed from a child during a tonsilectomy. The adenoid tissue was obtained from University of California at Los Angeles and frozen for future use. The frozen tissue was ground in a mortar and pestle and lysed immediately in buffer containing guanidinium isothiocyanate (cf. Chirgwin JM et al (1979) Biochemistry 18:5294). Lysis was followed by several phenol-chloroform extractions and ethanol precipitations. Poly-A+ mRNA was isolated using biotinylated oligo d(T) and streptavidin coupled to paramagnetic particles (Poly(A) tract isolation system; Promega, Madison, Wis.).

The poly A mRNA from the inflamed adenoid tissue was used by Stratagene Inc (La Jolla, Calif.) to construct a cDNA library. cDNA synthesis was primed using oligo dT and/or random hexamers. Synthetic adapter oligonucleotides were ligated onto cDNA ends enabling its insertion into the UNI-ZAP vector system (Stratagene Inc). This allows high efficiency unidirectional (sense orientation) lambda library construction and the convenience of a plasmid system with blue/white color selection to detect clones with cDNA insertions.

The quality of the each cDNA library was screened using either DNA probes or antibody probes, and then the PBLUESCRIPT phagemid (Stratagene Inc) was rapidly excised in living cells. The phagemid allows the use of a plasmid system for easy insert characterization, sequencing, site-directed mutagenesis, the creation of unidirectional deletions and expression of fusion proteins. Phage particles from each library were infected into the *E. coli* host strain XL1-BLUE (Stratagene Inc). The high transformation efficiency of XL1-BLUE increases the probability of obtaining rare, under-represented clones from the cDNA library.

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and created a smaller, single stranded circular phagemid DNA molecule that included all DNA sequences of the PBLUESCRIPT plasmid and the cDNA insert. The phagemid DNA was released from the cells and purified, then used to re-infect fresh bacterial host cells (SOLR, Stratagene Inc), where the double stranded phagemid DNA was produced. Because the phagemid carries the gene for β-lactamase, the newly transformed bacteria were selected on medium containing ampicillin.

Phagemid DNA was purified using the QIAWELL-8 plasmid purification system from QIAGEN DNA purification system (QIAGEN Inc, Chatsworth, Calif.). This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the inflamed adenoid library were sequenced in part. Methods for DNA sequencing are well known in the art. Conventional enzymatic methods employed DNA polymerase Klenow fragment, SEQUENASE DNA polymerase (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the CATALYST 800 DNA sequencer and the Applied Biosystems 373 DNA sequencer).

IV Homology Searching of cDNA Clones and Deduced Protein

Each sequence so obtained was compared to sequences in GenBank using a search algorithm developed by Applied Biosystems Inc. and incorporated into the INHERIT 670 sequence analysis system. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

The nucleotide and amino acid sequences for the adenoid expressed chemokine, ADEC are shown in FIG. 1.

V Identification and Full Length Sequencing of the Gene

From all of the randomly picked and sequenced clones of the inflamed adenoid library, adec sequences were homologous to, but clearly different from, any known C-X-C chemokine molecule. The nucleotide sequence for adec was found within Incyte clone 20293. When all three possible predicted translations of the sequence were searched against protein databases such as SwissProt and PIR, no exact matches were found to the possible translations of adec. FIG. 2 shows the comparison of ADEC with other a chemokine molecules; substantial regions of homology including the C-X-C motif are shaded. The phylogenetic analysis, however, (FIG. 3) shows that adec is not very closely related to other well characterized human C-X-C chemokines. The most related of these molecules cluster together at the right hand side of the figure. It appears that adec may represent a new subfamily or variant of the C-X-C chemokines.

VI Antisense Analysis

Knowledge of the correct, complete cDNA sequences of the novel expressed chemokine genes will enable their use in antisense technology in the investigation of gene function. Either oligonucleotides, genomic or cDNA fragments comprising the antisense strand of adec can be used either in vitro or in vivo to inhibit expression of the specific protein. Such technology is now well known in the art, and probes can be designed at various locations along the nucleotide sequence. By treatment of cells or whole test animals with such antisense sequences, the gene of interest can be effectively turned off. Frequently, the function of the gene can be ascertained by observing behavior at the cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of ADEC

Expression of adec may be accomplished by subcloning the cDNA into an appropriate expression vector and transfecting this vector into an appropriate expression host. In this particular case, the cloning vector previously used for the generation of the tissue library also provides for direct expression of the included sequence in E. coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated bacterial strain with IPTG using standard methods will produce a fusion protein corresponding to the first seven residues of β-galactosidase, about 15 residues of "linker," and the peptide encoded within the cDNA. Since CDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

Adec CDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as Saccharomyces cerevisiae, and bacteria such as E. coli. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts; or alpha factor, alcohol oxidase or PGH promoters for yeast. Transcription enhancers, such as the RSV enhancer, may be used in mammalian host cells. Once homogeneous cultures of recombinant cells are obtained through standard culture methods, large quantities of recombinantly produced ADEC can be recovered from the conditioned medium and analyzed using chromatographic methods known in the art.

VIII Isolation of Recombinant ADEC

ADEC may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp, Seattle, Wash.). The inclusion of a cleavable linker sequence (such as Factor XA or enterokinase) between the purification domain and the ADEC-encoding sequence may be useful to facilitate production of ADEC.

IX Production of ADEC-Specific Antibodies

Two approaches are utilized to raise antibodies to ADEC, and each approach is useful for generating either polyclonal or monoclonal antibodies. In one approach, denatured ADEC from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

Figure 4:
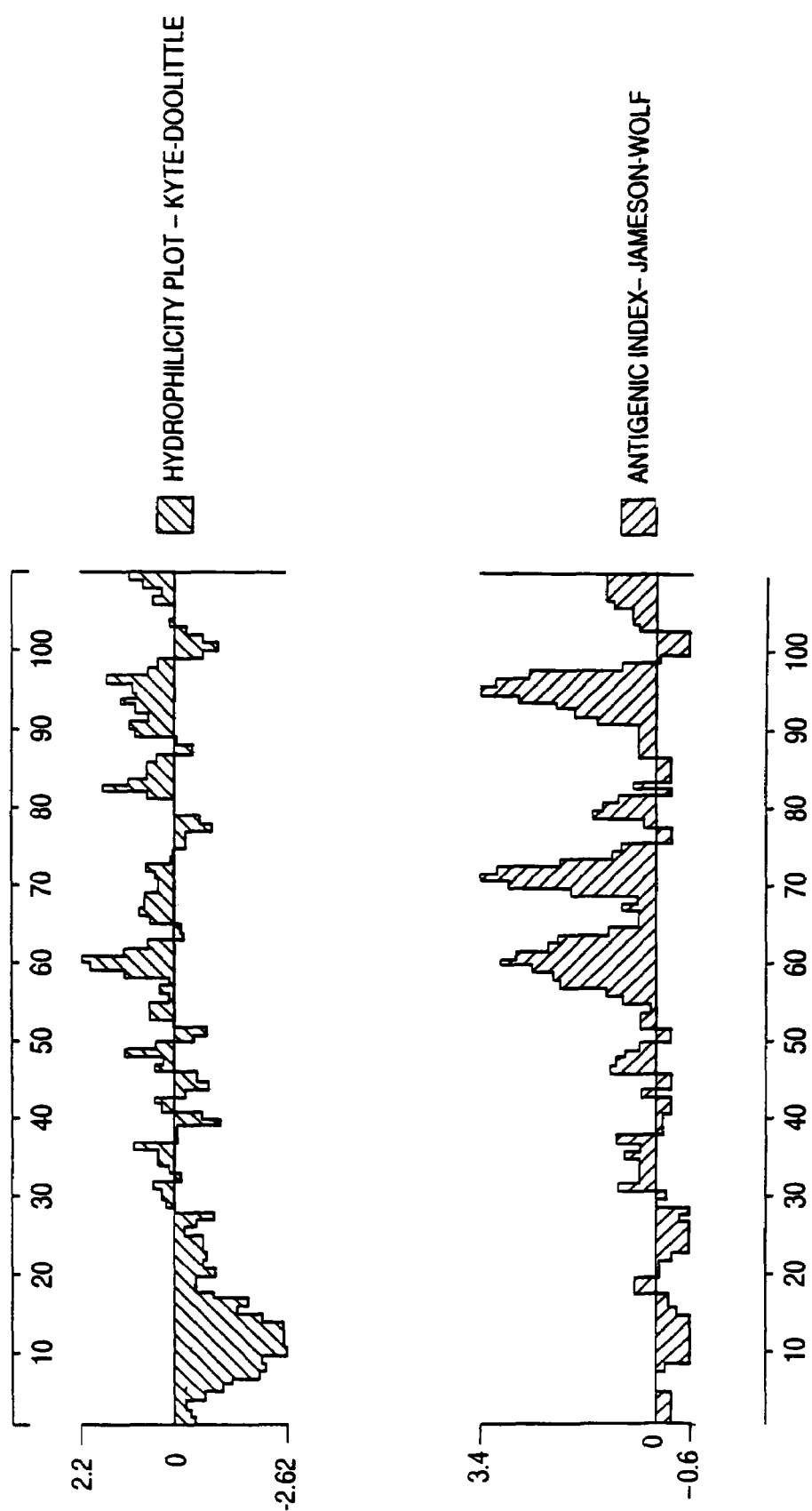
FIG. 4 displays an analysis of hydrophobicity and immunogenic characteristics of ADEC based on the predicted aa sequence and composition.

In the second approach, the amino acid sequence of ADEC, as deduced from translation of the cDNA, is analyzed to determine regions of high immunogenicity. Oligopeptides comprising hydrophilic regions, as shown in FIG. 4, are synthesized and used in suitable immunization protocols to raise antibodies. Analysis to select appropriate epitopes is described by Ausubel FM et al (1989, Current Protocols in Molecular Biology, Vol 2, John Wiley & Sons).

The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using a 431A peptide synthesizer (Applied Biosystems) using fmoc-chemistry and coupled to keyhole limpet hemocyanin (KLH, Sigma) by reaction with M-maleimidobenzoyl-N-hydroxysuccinimide ester (MBS; cf. Ausubel F M et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled ADEC to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled ADEC, 1 mg/ml. Clones producing antibodies will bind a quantity of labeled ADEC which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ or stronger, will typically be made by standard procedures as described in Harlow and Lane (1988) Antibodies: A Laboratory Manual, Cold Spring Harbor Laboratory, N.Y.; and in Goding (1986) Monoclonal Antibodies: Principles and Practice, 2nd Ed, Academic Press, New York, N.Y.; both incorporated herein by reference.

X Diagnostic Test Using ADEC-Specific Antibodies

Particular ADEC antibodies are useful for the diagnosis of prepathologic conditions, and chronic or acute diseases which are characterized by differences in the amount or distribution of ADEC. To date, ADEC has only been found in inflamed adenoid and is thus specific for abnormalities or pathologies of that tissue.

Diagnostic tests for ADEC include methods utilizing the antibody and a label to detect ADEC in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241.

Also, recombinant immunoglobulins may be produced as shown in U.S. Pat. No. 4,816,567, incorporated herein by reference.

A variety of protocols for measuring soluble or membrane-bound ADEC, using either polyclonal or monoclonal antibodies specific for that ADEC are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on ADEC is preferred, but a competitive binding assay may be employed. These assays are described, among other places, in Maddox, Del. et al (1983; J Exp Med 158:1211).

XI Purification of Native ADEC Using Specific Antibodies

Native or recombinant ADEC was purified by immunoaffinity chromatography using ADEC-specific antibodies. In general, an immunoaffinity column is constructed by covalently coupling the anti-ADEC antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE resin (Pharmacia LKB Biotechnology). The antibody is coupled to the resin, the resin is blocked, and the derivative resin is washed according to the manufacturer's instructions.

Such an immunoaffinity column was utilized in the purification of ADEC by preparing a fraction from cells containing ADEC in a soluble form. This preparation was derived by solubilization of the whole cell or of a subcellular fraction obtained via differential centrifugation by the addition of detergent or by other methods well known in the art. Alternatively, soluble ADEC containing a signal sequence may be secreted in useful quantity into the medium in which the cells are grown.

A soluble ADEC-containing preparation was passed over the immunoaffinity column, and the column was washed under conditions that allow the preferential absorbance of ADEC (eg, high ionic strength buffers in the presence of detergent). Then, the column was eluted under conditions that disrupt antibody/ADEC binding (e.g., a buffer of pH 2–3 or a high concentration of a chaotrope such as urea or thiocyanate ion), and the ADEC was collected.

XII Determination of ADEC-Induced Chemotaxis or Cell Activation

The chemotactic activity of ADEC is measured in a 48-well microchemotaxis chamber (Falk W R et al (1980) J Immunol Methods 33:239). In each well, two compartments are separated by a filter that allows the passage of cells in response to a chemical gradient. Cell culture medium such as RPMI 1640 containing ADEC is placed on one side of a filter, usually polycarbonate, and cells suspended in the same media are placed on the opposite side of the filter. Sufficient incubation time is allowed for the cells to traverse the filter in response to the concentration gradient across the filter. Filters are recovered from each well, and cells adhering to the side of the filter facing ADEC are typed and quantified.

The specificity of the chemoattraction is determined by performing the chemotaxis assay on specific populations of cells. First, blood cells obtained from venipuncture are fractionated by density gradient centrifugation and the chemotactic activity of ADEC is tested on enriched populations of neutrophils, peripheral blood mononuclear cells, monocytes and lymphocytes. Optionally, such enriched cell populations are further fractionated using $CD8^+$ and $CD4^+$ specific antibodies for negative selection of $CD4^+$ and $CD8^+$ enriched T-cell populations, respectively.

Another assay elucidates the chemotactic effect of ADEC on activated T-cells. There, unfractionated T-cells or fractionated T-cell subsets are cultured for 6 to 8 hours in tissue culture vessels coated with CD-3 antibody. After this CD-3 activation, the chemotactic activity of ADEC is tested as described above. Many other methods for obtaining enriched cell populations are known in the art.

Some chemokines also produce a non-chemotactic cell activation of neutrophils and monocytes. This is tested via standard measures of neutrophil activation such as actin polymerization, increase in respiratory burst activity, degranulation of the azurophilic granule and mobilization of $Ca^{++}$ as part of the signal transduction pathway. The assay for mobilization of $Ca^{++}$ involves preloading neutrophils with a fluorescent probe whose emission characteristics have been altered by $Ca^{++}$ binding. When the cells are exposed to an activating stimulus, $Ca^{++}$ flux is determined by observation of the cells in a fluorometer. The measurement of $Ca^{++}$ mobilization has been described in Grynkievicz G et al. (1985) J Biol Chem 260:3440; and McColl S et al. (1993) J Immunol 150:4550–4555, incorporated herein by reference.

Degranulation and respiratory burst responses are also measured in monocytes (Zachariae C O C et al. (1990) J Exp Med 171:2177–2182). Further measures of monocyte activation are regulation of adhesion molecule expression and cytokine production (Jiang Y et al. (1992) J Immunol 148:2423–2428). Expression of adhesion molecules also varies with lymphocyte activation (Taub D et al. (1993) Science 260:355–358).

XII Drug Screening

This invention is particularly useful for screening compounds by using ADEC polypeptide or binding fragment thereof in any of a variety of drug screening techniques.

The ADEC polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between ADEC or fragment and the agent being tested or examine the diminution in complex formation between ADEC and a neutrophil or fibroblast caused by the agent being tested.

Thus, the present invention provides methods of screening for drugs or any other agents which can affect inflammation and disease. These methods comprise contacting such an agent with an ADEC polypeptide or fragment thereof and assaying (i) for the presence of a complex between the agent and the ADEC polypeptide or fragment, or (ii) for the presence of a complex between the ADEC polypeptide or fragment and the cell, by methods well known in the art. In such competitive binding assays, the ADEC polypeptide or fragment is typically labeled. After suitable incubation, free ADEC polypeptide or fragment is separated from that present in bound form, and the amount of free or uncomplexed label is a measure of the ability of the particular agent to bind to ADEC or to interfere with the ADEC/cell complex.

Another technique for drug screening provides high throughput screening for compounds having suitable binding affinity to the ADEC polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with ADEC polypeptide and washed. Bound ADEC polypeptide is then detected by methods well known in the art. Purified ADEC can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding ADEC specifically compete with a test compound for binding to ADEC polypeptide or fragments thereof. In this manner, the antibodies can be used to detect the presence of any peptide which shares one or more antigenic determinants with ADEC.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf. Hodgson J (1991) Bio/Technology 9:19–21; incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous chemokine-like molecules or to identify efficient inhibitors. Useful examples of rational drug design may include molecules which have improved activity or stability as shown by Braxton S and Wells J A (1992; Biochemistry 31:7796–7801) or which act as inhibitors, agonists, or antagonists of native peptides as shown by Athauda S B et al (1993; J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as x-ray crystallography. In addition, knowledge of the ADEC amino acid sequence provided herein will provide guidance to those employing computer modeling techniques in place of or in addition to x-ray crystallography.

XV Identification of ADEC Receptors

Purified ADEC is useful for characterization and purification of specific cell surface receptors and other binding molecules. Cells which respond to ADEC by chemotaxis or other specific responses are likely to express a receptor for ADEC. Radioactive labels may be incorporated into ADEC by various methods known in the art. A preferred embodiment is the labeling of primary amino groups in ADEC with $^{125}$I Bolton-Hunter reagent (Bolton A E and Hunter W M (1973) Biochem J 133:529–539), which has been used to label other chemokines without concomitant loss of biological activity (Hebert C A et al (1991) J Biol Chem 266:18989; McColl S et al (1993) J Immunol 150:4550–4555). Receptor-bearing cells are incubated with labeled ADEC. The cells are then washed to removed unbound ADEC, and receptor-bound ADEC is quantified. The data obtained using different concentrations of ADEC are used to calculate values for the number and affinity of receptors.

Labeled ADEC is useful as a reagent for purification of its specific receptor. In one embodiment of affinity purification, ADEC is covalently coupled to a chromatography column. Receptor-bearing cells are extracted, and the extract is passed over the column. The receptor binds to the column by virtue of its biological affinity for ADEC. The receptor is recovered from the column and subjected to N-terminal protein sequencing. This amino acid sequence is then used to design degenerate oligonucleotide probes for cloning the receptor gene.

In an alternate method, expression cloning, mRNA is obtained from receptor-bearing cells and made into a cDNA expression library. The library is transfected into a population of cells, and those cells in the population which express the receptor are selected using fluorescently labeled ADEC. The receptor is identified by recovering and sequencing recombinant DNA from highly labeled cells.

In another alternate method, antibodies are raised against the surface of receptor-bearing cells, specifically monoclonal antibodies. The monoclonal antibodies are screened to identify those which inhibit the binding of labeled ADEC. These monoclonal antibodies are then used in affinity purification or expression cloning of the receptor.

Soluble receptors or other soluble binding molecules are identified in a similar manner. Labeled ADEC is incubated with extracts or other appropriate materials derived from inflamed adenoid. After incubation, ADEC complexes larger than the size of purified ADEC are identified by a sizing technique such as size exclusion chromatography or density gradient centrifugation and are purified by methods known in the art. The soluble receptors or binding protein(s) are subjected to N-terminal sequencing to obtain information sufficient for database identification, if the soluble protein is known, or cloning, if the soluble protein is unknown.

XVI Use and Administration of ADEC

Antibodies, inhibitors, receptors or analogs of ADEC (treatments for excessive ADEC production, hereafter abbreviated TEC), can provide different effects when administered therapeutically. TECs will be formulated in a non-toxic, inert, pharmaceutically acceptable aqueous carrier medium preferably at a pH of about 5 to 8, more preferably 6 to 8, although the pH may vary according to the characteristics of the antibody, inhibitor, receptor or analog being formulated and the condition to be treated. Characteristics of the TEC include solubility of the molecule, half-life and antigenicity/immunogenicity and may aid in defining an effective carrier. Native human proteins are preferred as TECs, but organic molecules resulting from drug screens may be equally effective in particular situations.

TECs may be delivered by known routes of administration including but not limited to topical creams or gels; transmucosal spray or aerosol, transdermal patch or bandage; injectable, intravenous or lavage formulations; or orally administered liquids or pills. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include disease state (e.g. severity) of the patient, age, weight, gender, diet, time of administration, drug combination, reaction sensitivities, and tolerance/response to therapy. Long acting TEC formulations might be administered every 3 to 4 days, every week, or once every two weeks depending on half-life and clearance rate of the particular TEC.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TECs and that administration targeting the adenoid may necessitate delivery in a manner different from that for delivery targeted to a more internal tissue.

It is contemplated that conditions or diseases of the adenoids which activate, fibroblasts, neutrophils or other leukocytes may precipitate permanent damage that is treatable with TECs. These conditions or diseases may be specifically diagnosed by the tests discussed above, and such testing should be performed in suspected cases of Epstein-Barr virus, Hodgkin's disease, various neoplasms or nonspecific pharyngitis.

All publications and patents mentioned in the above specification are herein incorporated by reference. The foregoing written specification is considered to be sufficient to enable one skilled in the art to practice the invention. Indeed, various modifications of the above described modes for carrying out the invention which are obvious to those skilled in the field of molecular biology or related fields are intended to be within the scope of the following claims.

What is claimed is:

1. An isolated human antibody or other antigen-specific binding molecule which specifically binds to a polypeptide comprising SEQ ID NO:2, wherein the antigen-specific binding molecule is selected from the group consisting of a single chain antibody, an Fab fragment, and an F(ab')2 fragment.

2. The isolated human antibody of claim 1, wherein said antibody is a neutralizing antibody.

3. The isolated human antibody of claim 1, wherein said antibody is a polyclonal antibody.

4. The isolated human antibody of claim 1, wherein said antibody is a monoclonal antibody.

5. A composition comprising the antibody or antigen-specific binding molecule of claim 1 and an acceptable excipient.

6. The composition of claim 5, wherein the antibody or antigen-specific binding molecule is labeled.

7. The composition of claim 5, wherein said label is selected from the group consisting of radionuclides, enzymes, substrates, cofactors, inhibitors, fluorescent agents, chemiluminescent agents and magnetic particles.

8. The antibody of claim 4, wherein said antibody has an affinity of at least $10^8$ $M^{-1}$.

9. The antibody of claim 8, wherein said antibody has an affinity of at least $10^9$ $M^{-1}$.

10. The antibody of claim 9, wherein said antibody has an affinity of at least $10^{10}$ $M^{-1}$.

* * * * *